United States Patent [19]

Lucas et al.

[11] 4,252,443
[45] Feb. 24, 1981

[54] BLACKENING SENSOR

[75] Inventors: John M. Lucas, Montreal; Serge Gracovetsky, St. Lambert, both of Canada

[73] Assignee: Domtar Inc., Montreal, Canada

[21] Appl. No.: 65,287

[22] Filed: Aug. 9, 1979

[51] Int. Cl.³ .......................................... G01N 21/47
[52] U.S. Cl. .................................. 356/430; 250/562; 356/446
[58] Field of Search .............. 356/429, 430, 445, 446, 356/448; 250/559, 562, 571, 572

[56] References Cited

U.S. PATENT DOCUMENTS

| 3,345,908 | 10/1967 | Jensen | 356/445 |
| 4,019,066 | 4/1977 | Lucas et al. | 356/445 |
| 4,092,068 | 5/1978 | Lucas et al. | 356/446 |

Primary Examiner—R.A. Rosenberger

[57] ABSTRACT

A blackening sensor analyses a signal generated by the detection of scattered light reflected from a succession of small illuminated areas on the surface of a web to determine the degree of skewness of the amplitude distribution of the generated signal from a normal distribution, thereby to provide an indication of the degree of blackening.

9 Claims, 12 Drawing Figures

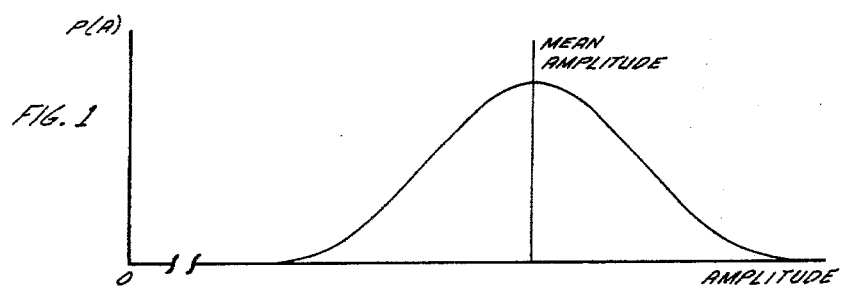
FIG. 1
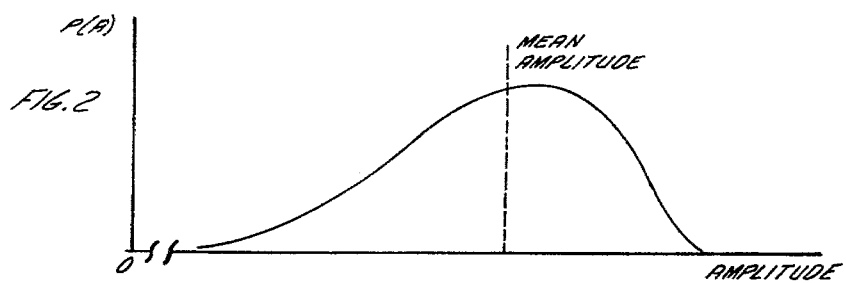
FIG. 2
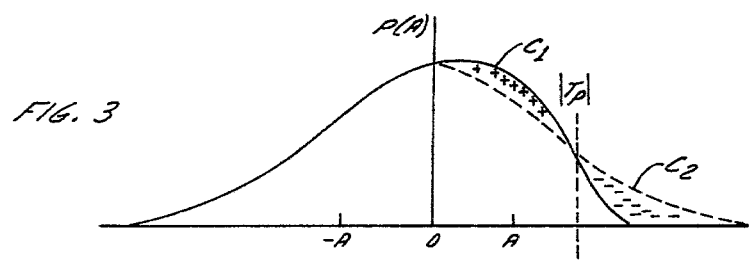
FIG. 3
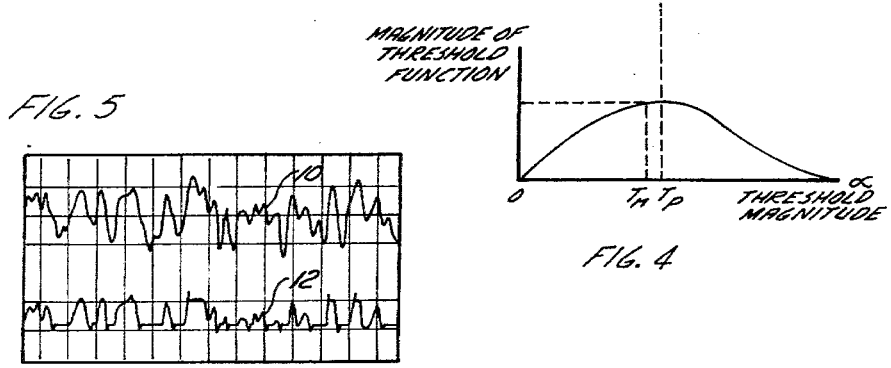
FIG. 5
FIG. 4

BLACKENING SENSOR

FIELD OF THE INVENTION

The present invention relates to a blackening sensor. More specifically the present invention relates to the on-line detection and/or measurement of blackening.

BACKGROUND TO THE INVENTION

Blackening is a defect in a paper sheet related to the formation of discrete areas of relatively smooth surface texture during the manufacturing of newsprint. Blackened areas of interest are generated by calendering and have a darkened appearance under certain viewing conditions. Blackening is normally associated with areas of relatively high moisture content, but a direct correlation between moisture content and blackening is not likely to be achieved primarily because it is believed moisture is just one factor that contributes significantly to blackening.

No on-line equipment is available or has been devised for the measurement of blackening. In fact, it is believed that there are no detectors of any kind adapted to sense blackening. The phenomena is simply observed by the naked eye and the quality of the paper is determined by subjective judgement.

It has been proposed to examine the surface topography of a travelling paper web and to determine the topographic profile and the amount of dirt on the paper web, utilizing the technology described in U.S. Pat. No. 4,092,068 issued May 30, 1978 to Lucas and Gracovetsky. This patent discloses a sensor head wherein scattered light reflected from small illuminated areas on the surface of the travelling web are detected by a pair of detectors and added to obtain a dirt signal substantially free of topography or subtracted to obtain a topographic signal substantially free of dirt. The dirt signal provides the best indication of blackening when analysed in accordance with the teachings herein.

BRIEF DESCRIPTION OF THE INVENTION

Broadly the present invention relates to a blackening sensor comprising means to direct light onto the surface of travelling web thereby to illuminate a succession of spots on the surface of the web; means to continuously detect scattered light reflected from said spots on said web and convert said detected light into electrical signals; means for analysing said signals so as to obtain an indication of skewness of the probability density function of the amplitude of said signal to obtain an indication of the degree of blackening said web.

BRIEF DESCRIPTION OF THE DRAWINGS

Further features, objects and advantages will be evident from the following detailed description of the preferred embodiments of the present invention when taken in conjunction with the accompanying drawings in which:

FIG. 1 is a typical plot of the probability density function of the amplitude of the electrical signal generated by detecting scattered light from paper.

FIG. 2 is a typical plot indicating the asymmetry of the probability density function of the amplitude of scattered light from a blackened sheet of paper.

FIG. 3 is a plot similar to FIG. 2 but wherein the mean amplitude of the signal has been designated as the origin and the average magnitude of the signal (i.e. average of the rectified signal) has been normalized to a constant magnitude A to eliminate the effect arising from average magnitude variation without significantly affecting the symmetry of the distribution. The drawing has been further modified by reflecting the negative part ($C_2$) of the probability density function of the amplitude about the origin on to the positive part ($C_1$) of the probability density function to emphasize the lack of symmetry of the probability density function.

FIG. 4 is a plot of the integral of the differences between function $C_1$ and $C_2$ of FIG. 3 in the interval 0 to infinity.

FIG. 5 indicates a comparison of signal before and after clipping.

DETAILED DESCRIPTION OF THE PREFERRED EMBODIMENTS

Figure 7:
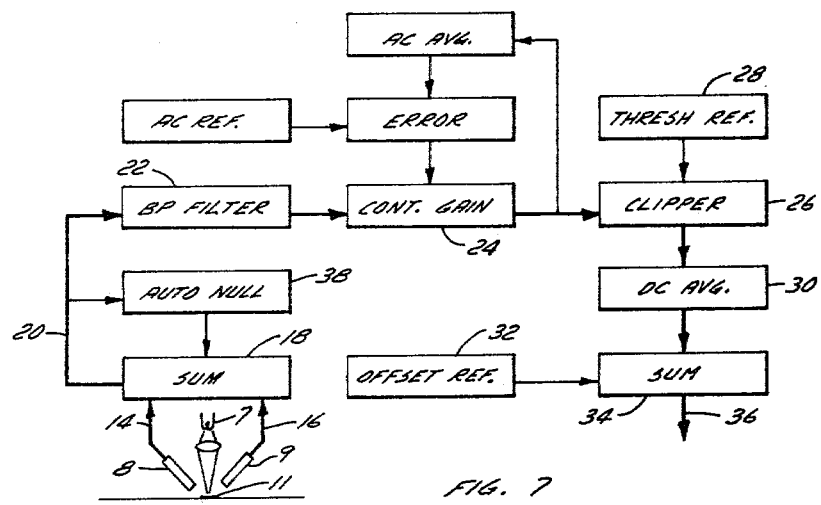
FIG. 7 is a block diagram of the preferred blackening sensor circuit.

In accordance with the present invention the blackening measurement is derived from signals generated by the sensor of the said United States patent. It is obtained by processing the sum of any pair of detectors which describe the variation in intensity of the scattered light reflected from a succession of illuminated spots less than 1 mm in diameter, while at the same time minimizing the effect of topography. The preferred arrangement utilizes a pair of detectors in the manner described in the said patent, obviously a single detector detecting scattered light may be used however the accuracy of the operation may be impaired and in some cases it may be very difficult to properly distinguish blackening.

Blackened areas on the paper are distinguished by changes in the skewness of the probability density function of the signal amplitude (hereinafter referred to as P(A) see FIGS. 2 and 3). For example, FIG. 1 shows variations in intensity of scattered light reflected from a sheet of paper having no blackening defects. The curve illustrated is for a paper having a substantially symetrical P(A). Generally non blackened paper exhibits a degree of skewness in the signal generated so that only those areas with higher skewness than the other parts of the web are considered as potential areas of high probability of blackening.

In general in a blackened area the skewness of P(A) will increase somewhat for example as indicated in FIG. 2 so that the mean amplitude which by definition divides the P(A) in two equal areas is now shifted to the left with respect to the position it had in FIG. 1. For paper having the type of P(A) shown in FIG. 1 this shift is to the left of the peak. It is believed this occured since the development of blackening tends to increase the probability of low amplitude scattering without any corresponding effect on the high amplitude side of the distribution. Quantifying the variations in skewness or asymmetry of P(A) signal generated by the scattered light therefore may be used to generate a signal representative of degree of blackening.

FIG. 3 is FIG. 2 revised to have the mean amplitude (average of the unrectified signal) as the origin 0 and the average magnitude of the signal (average of rectified signal) normalized to a constant amplitude A to eliminate the effects arising from average rectified amplitude variation. By reflecting the negative part of the amplitude distribution about the origin as indicated by the dash lines $C_2$ to superimpose over $C_1$ which is P(A) in the interval 0 to infinity, it is clear that for amplitudes less than Tp, $C_1$ exceeds $C_2$ and similarly for amplitudes above Tp, $C_2$ exceeds $C_1$. Thus two equal areas are enclosed between the lines $C_1$ and $C_2$.

For example, suppose the signal is clipped symmetrically at a threshold amplitude $\pm$ A with respect to a reference value which is zero. The corresponding P(A) for that clipped signal is derived from the previous P(A) for the unclipped signal in the interval $\pm$ A. The origin 0 was the mean amplitude of the non clipped signal, but in general there is no reason why the clipped P(A) will still have the same mean amplitude because of the lack of symmetry of P(A) hence the concept that the shift in mean amplitude of clipped and non-clipped is related to the asymetry of P(A).

If A = o, the position of the mean amplitude will not vary for the clipped and non-clipped signal. Similarly if A = infinity the same conclusion applies. However for some intermediate value, the mean will vary.

A plot of the change of mean amplitude versus A is given in FIG. 4. It will be noted the function starts from 0 and ends at 0 and therefore must have at least one extremum. In the example shown in FIG. 4 the extremum is located at the intersection of $C_1$ and $C_2$. Thus the integral of ($C_1$–$C_2$) plotted in FIG. 4 is related to the change in mean amplitude.

It is preferred to maximize the portion of the signal that indicates skewness and therefore the operating threshold amplitude Tm is chosen preferably in the vicinity of Tp since the difference between the mean of the whole signal and of the clipped signal will be the largest (see FIG. 4).

In other words, the mean amplitude of the full signal as indicated by the line 10 in FIG. 5 is obtained by averaging the unrectified signal to find the origin 0 of the overall signal generated by sensing the scattered light from the surface. This signal is then clipped using Tm the clipping voltage as indicated at 12 in FIG. 5 to produce a second signal that contains only a portion of the first signal 10. The mean amplitude of the second signal 12 is then obtained and the difference between the mean of signal 10 and the mean of signal 12 provides the indication of blackening.

This obtaining of the mean, clipping, obtaining a second mean and comparing the means takes place continuously over discrete periods of time. Such time periods being normally adjusted in accordance with the rate of transverse movement of the sensor as it is scans across the web and the desired cross machine resolution.

Figure 6:
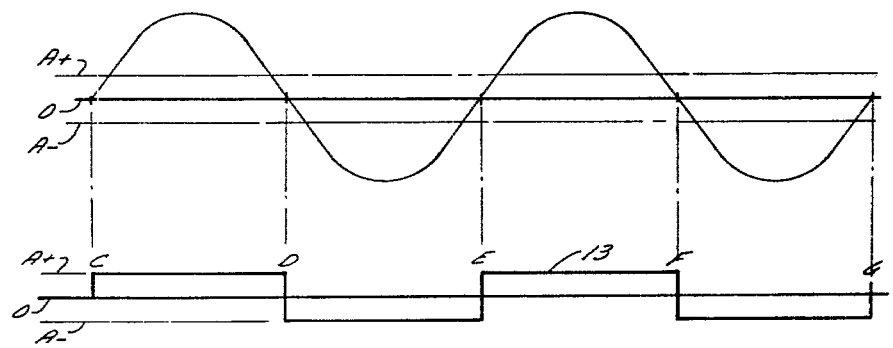
FIG. 6 illustrates yet another way of determining the degree of skewness of the signal.

In yet another way of analysing the signal generated using electronic techniques is to again obtain the mean of the overall signal generated, in effect clip the signal generated and measure the time span the clipped signal is above or below the average or threshold value of the overall signal, thereby to give an indication of a degree of the skewness as indicated in FIG. 6. For that illustration the time above the datum line 0 for the whole signal is related to the area between C & D, E & F etc and the datum line 0 while the time below would be similarly be related to the areas between D & E and F & G and the datum line 0. The areas will be equal for the whole signal, however clipping the signal as indicated at 13 in FIG. 6 and using the datum line for the whole signal imbalances these areas and the degree of imbalance is an indication of the skewness of the signal or blackening. In actual practice it is sufficient to measure the time during which the signal is above the preset plus threshold amplitude and the time it is below the preset minus threshold amplitude and compare these times. The time must be measured accurately in the order of about a micro second.

It will be apparent from the above that the indication of blackening is generated by the change in the third moment of P(A) and any means for approximating the third moment of the signal should provide an indication of blackening.

Referring to FIG. 7, the electronics of the present invention have been illustrated by blocks with the heavy lines emphasising the principal signal path. The output from the two detectors 8 and 9 as indicated by the lines 14 & 16 i.e. the signals representative of scattered light reflected from the succession of spots 11 illuminated by light source 7 and preferably less than 1 mm in diameter on the surface of the paper are summed in the summation device indicated at 18 (as above indicated a single detector may be used and obviously there need be no summing of the signal). In any event, the summed signal in line 20 passes through a band filter 22 and a control gain amplifier 24 is employed in a closed loop to normalize the resultant signal to a constant AC average determined by the voltage AC reference. The clipping device 26 clips the signal at a level set by the clip reference voltage Tm as defined by the threshold reference 28. The average or mean of the clipped signal for the discrete time periods described above is determined as indicated at 30 and the average DC signal so provided is then added to an off-set reference voltage 32 in the summer 34 to ensure that the blackening output signal remains positive and at a convenient range for process and control computer manipulation.

It is essential to operate in a frequency which is large enough to include harmonics which characterize the skewness of P(A).

If we assume blackened areas spaced ¼" and a machine speed of 1700 ft/min the blackened spots crossing the sensor generate a fundamental frequency of about 1.4 KH$_z$. However, only the harmonic content of this signal may skew its amplitude distribution, skewing of the sensor signal depends also on the relative phase of the harmonic to the fundamental. Thus the 1.4 KH$_z$ signal must be supplemented by at least a single harmonic of 2.8 KH$_z$ and a 45° relative phase shift in the fundamental eliminates the skewness altogether. Thus the sensor circuitry must propagate both fundamental and harmonic frequencies and do so without causing phase shifts to either. The above condition must be satisfied over the frequency transpositions accompanying machine speed changes.

The circuitry is designed to respond to small changes in input signal symmetry and obviously therefore it must itself accurately preserve the symmetry or lack thereof of such signal. If symmetry distortions do occur and it is important that they be detected and held to a minimum.

As above indicated the size of the illuminated area preferably is 1 mm or less. The time for averaging or the amount of signal continuously being analyzed to determine blackening is generally at least 1/25 of second but if too low the measurement may be degraded.

The Auto Null block 38 after the circuit summer 18 provides a periodic circuit standardization to compensate for effects of temperature and other long term drifts by automatically feeding a highly symetric reference signal through the circuitry when the sensor is off web contact at the extremity of its travel across the web assuming the sensor is mounted to traverse the web. Circuit drifts will be revealed in output changes which will be measured and stored for correction purposes by the computer during its periodic calibration routine.

Results of operation utilizing the present invention on-line on a newsprint machine are illustrated in FIGS. 8 to 12.

Figure 8:
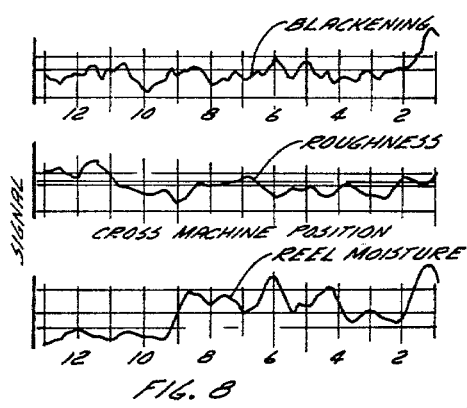
FIG. 8 is a cross-machine profile of blackening, roughness and reel moisture from a test conducted according to the present invention.

FIG. 8 shows the blackening profile and roughness profile as determined utilizing the above described patented sensor head and the present invention and the reel moisture as determined utilizing the standard moisture gauge. Blackening only is indicated at one point (which in this particular case coincided with peak moisture) and an examination of the paper indicated blackening while not severe only occurred at this location on the reel.

Figure 9:
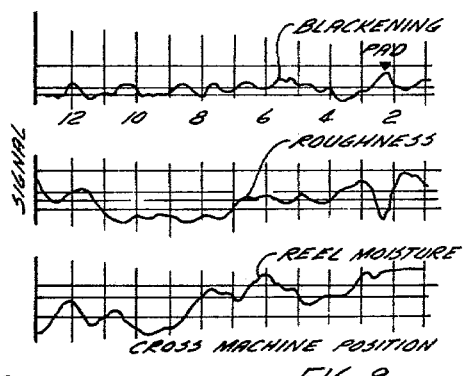
FIG. 9 is a profile similar to FIG. 8 showing the effect of application of a pad to the calendar stack on blackening, roughness and moisture.
Figure 10:
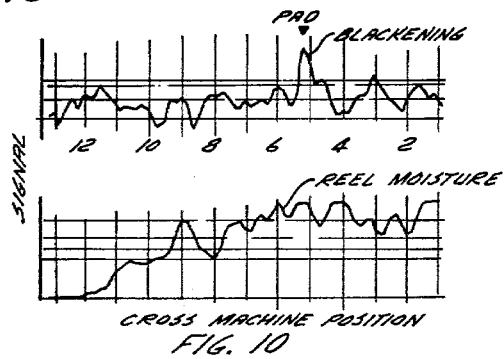
FIG. 10 is a view similar to FIG. 9 but illustrating the application of a pad in another location and showing the relation of the blackening to reel moisture and FIGS. 11 and 12 illustrate the complexity of the relationship between blackening, roughness and moisture.

The profile of FIG. 9 shows the effect of applying a pad to the calendar position of high moisture near the front of the machine. It will be noted that the roughness is reduced i.e. the sheet becomes smoother where the pad is applied while the blackening profile shows its highest value at this point. Subsequent inspection of the paper showed blackening at, and only at the position of the pad. A similar experiment was carried out with the pad being applied at slice or position no. 5 as shown in FIG. 10. Examination of the paper produced indicated blackening at slice 5 and a slight degree of blackening at other positions between slice 6 in the front of the machine, especially near slice 3.

Figure 11:
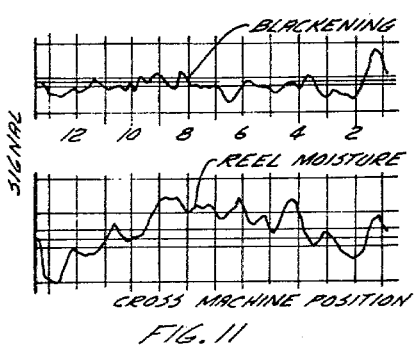

FIG. 11 indicates a blackening streak along the front edge of the paper at slice 1 to 2, while other positions had no visible indication of blackening nor did it show up on the blackening sensor. It is apparent that the reel moisture was high in many locations transversely of the web but the high level of moisture did not always result in blackening thereby indicating the inadequacy of peak moisture control strategy to control the machine and avoid blackening.

Figure 12:
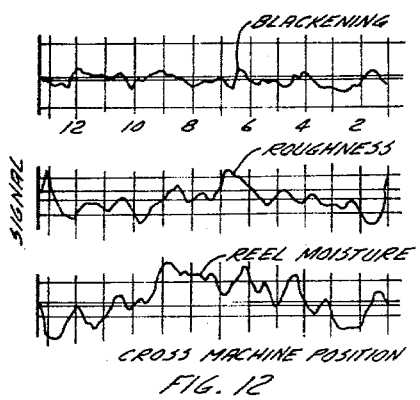

FIG. 12 compares blackening with the roughness value as sensed by the said patent and with moisture. FIG. 12 demonstrates that blackening occured at the front of the paper machine in a position where the moisture content was 1.6% below the moisture profile maximum with no other blackening indicated or visable on later inspection of the sheet.

One of the fundamental problems of on-line evaluation of blackening sensor is sampling. Obviously, machine direction variations are considerable and the degree of blackening may vary in a few feet of paper so that finding a representative sample can pose a problem.

Of primary interested is blackening at or below the level at which it becomes objectionable in a finished product and it is at such levels that the problems are most difficult if one is to apply a systematic valuation technique such as allpairs ranking. However, the evidence points to the sensor being sensitive and at sufficiently low blackening levels to permit close loop application.

There are long term shifts or changes in the base line generated by unblackened paper which will require periodic resetting of the set point that is representative of a particular degree of blackening.

While the disclosure has described clipping at equal amplitudes on opposite sides of the datum this is not essential and the circuitry can be modified to accomodate some differences between the positive and negative clipping amplitudes. Modifications may be made without departing from the spirit of the invention as defined in the appended claims.

We claim:

1. A blackening sensor comprising means to direct light onto the surface of a travelling paper web, thereby to illuminate a succession of spots on the surfaces of the web; means to continuously detect scattered light reflected from said spots and convert said detected light into electrical signals; means for analysing said signals to determine the degree of skewness of the probability density function of the amplitude of said electrical signals to obtain an indication of degree of blackening said web.

2. A blackening sensor as defined in claim 1 wherein said means for determining skewness of said signal includes means for clipping said signal.

3. A blackening sensor as defined in claim 1 wherein said means for determining skewness further comprises means for averaging said signals to obtain a first datum; means for clipping said signal at equal amplitudes on opposite side of said datum; means for averaging said clipped signal to find a second datum, means for determining the shift from said first datum to said second datum thereby to provide an indication of degree of blackening of said web.

4. A blackening sensor as defined in claim 1 wherein said means for analysing comprises means for comparing the time said signal is above a set positive threshold amplitude and the time said signal is below a set negative threshold amplitude.

5. A blackening sensor as defined in claim 1, 2, 3 or 4 wherein said means for detecting comprises a pair of detectors adapted to receive scattered light reflected from a pair of opposite sides of said illuminated spots.

6. A blackening sensor as defined in claim 1, 2, 3, or 4 wherein said spots are no greater the 1 mm in diameter and wherein said means for detecting comprises a pair of detectors adapted to detect scattered light reflected to a pair of opposite sides of said illuminated spots said opposite sides being positioned on the sides of said spots substantially perpendicular to the direction of travel of said web.

7. An apparatus for determining the degree of blackening of a travelling paper web comprising means to direct light onto the surface of said web thereby to illuminate succession of spots on the surface of said web; means for detecting non-specular light reflected from said illuminated spots; means for converting the detected light into electrical signals and means for determining the third moment of the distribution of the amplitudes of said electrical signals thereby to obtain an indication of the degree of blackening of said surface.

8. A method of determining the degree of blackening of the surface of a travelling paper web comprising illuminating a succession of spots no greater than 1 mm in diameter on the surface of said web, detecting scattered light reflected from said spots, converting the detected scattered light into electrical signals, measuring the degree of skewness of the distribution of the amplitude of said electrical signals from a normal distribution thereby to obtain an indication of the degree of blackening of said web.

9. A method as defined in claim 8 wherein said measuring comprises averaging said signals to obtain a first datum, clipping said signal at equal amplitude on opposite sides of said datum, averaging said clipped signal to find a second datum and measuring the shift from said datum to said second datum thereby to provide an indication of the degree of blackening of said web.

* * * * *